US008670037B2

(12) United States Patent
Arnon et al.

(10) Patent No.: US 8,670,037 B2
(45) Date of Patent: Mar. 11, 2014

(54) SYSTEM AND METHOD FOR REGISTRATION OF IMAGING DATA

(75) Inventors: Israel B. Arnon, Neve Tsuf (IL); Ori Elan, Tel-Aviv (IL)

(73) Assignee: Real Imaging Ltd., Lod (IL)

( * ) Notice: Subject to any disclaimer, the term of this patent is extended or adjusted under 35 U.S.C. 154(b) by 464 days.

(21) Appl. No.: 12/811,097

(22) PCT Filed: Dec. 28, 2008

(86) PCT No.: PCT/IL2008/001683
§ 371 (c)(1),
(2), (4) Date: Jun. 29, 2010

(87) PCT Pub. No.: WO2009/083973
PCT Pub. Date: Jul. 9, 2009

(65) Prior Publication Data
US 2010/0284591 A1 Nov. 11, 2010

Related U.S. Application Data

(60) Provisional application No. 61/006,223, filed on Dec. 31, 2007.

(51) Int. Cl.
*H04N 5/30* (2006.01)

(52) U.S. Cl.
USPC .......... 348/162

(58) Field of Classification Search
USPC .......... 348/162, 47; 382/128, 293, 285
See application file for complete search history.

(56) References Cited

U.S. PATENT DOCUMENTS

| | | | | |
|---|---|---|---|---|
| 5,946,425 | A * | 8/1999 | Bove et al. | 382/294 |
| 5,961,466 | A | 10/1999 | Anbar | |
| 6,094,198 | A | 7/2000 | Shashua | |
| 6,167,151 | A * | 12/2000 | Albeck et al. | 382/154 |
| 6,201,541 | B1 | 3/2001 | Shalom et al. | |
| 6,442,419 | B1 | 8/2002 | Chu et al. | |
| 6,701,081 | B1 | 3/2004 | Dwyer et al. | |
| 6,765,607 | B2 | 7/2004 | Mizusawa et al. | |
| 6,801,257 | B2 | 10/2004 | Segev et al. | |
| 6,850,862 | B1 | 2/2005 | Chidichimo et al. | |
| 6,965,690 | B2 | 11/2005 | Matsumoto | |
| 7,072,504 | B2 | 7/2006 | Miyano et al. | |

(Continued)

FOREIGN PATENT DOCUMENTS

| | | |
|---|---|---|
| DE | 10150918 | 5/2003 |
| GB | 2358752 | 8/2001 |

(Continued)

OTHER PUBLICATIONS

Author: Gerson Linck Bichinho Title: A Computer Tool for the Fusion and Visualization of Thermal and Magnetic Resonance Images Date: Aug. 14, 2007.*
Author: Gerson Linck Bichinho Title: A computer tool for the fsion and visualization of thermal and magnetic resonance images Date: Aug. 14, 2007.*
Communication Pursuant to Article 94(3) EPC Dated Dec. 21, 2010 From the European Patent Office Re. Application No. 08866783.7.

(Continued)

*Primary Examiner* — Andy Rao
*Assistant Examiner* — Jared Walker

(57) ABSTRACT

A method of obtaining imaging data from a tissue region is provided. The method is effected by associating imaging data with a surface contour of the tissue region and utilizing a model of contour changes in the tissue region to transform the data to reflect changes in the surface contour.

10 Claims, 4 Drawing Sheets
(1 of 4 Drawing Sheet(s) Filed in Color)

(56) References Cited

U.S. PATENT DOCUMENTS

| | | | | |
|---|---|---|---|---|
| 7,292,719 | B2 | 11/2007 | Arnon | |
| 2001/0046316 | A1 | 11/2001 | Miyano et al. | |
| 2004/0151365 | A1 * | 8/2004 | An Chang et al. | 382/154 |
| 2004/0236225 | A1 | 11/2004 | Murphy et al. | |
| 2005/0096515 | A1 | 5/2005 | Geng | |
| 2006/0285731 | A1 * | 12/2006 | Jiang et al. | 382/128 |
| 2007/0051889 | A1 | 3/2007 | Yannacone et al. | |
| 2007/0166284 | A1 | 7/2007 | Rasmussen et al. | |
| 2007/0213617 | A1 | 9/2007 | Berman et al. | |
| 2007/0293792 | A1 | 12/2007 | Sliwa et al. | |

FOREIGN PATENT DOCUMENTS

| | | |
|---|---|---|
| JP | 2007-525244 | 9/2007 |
| WO | WO 2004/098392 | 11/2004 |
| WO | WO 2006/003658 | 1/2006 |
| WO | WO 2009/083973 | 7/2009 |
| WO | WO 2009/083974 | 7/2009 |
| WO | WO 2009/118721 | 10/2009 |

OTHER PUBLICATIONS

International Search Report Dated Apr. 14, 2009 From the International Searching Authority Re.: Application No. PCT/IL2008/001684.

International Search Report Dated May 18, 2009 From International Searching Authority Re.: Application No. PCT/IL2008/001685.

Written Opinion Dated Apr. 14, 2009 From the International Searching Authority Re.: Application No. PCT/IL2008/001684.

Written Opinion Dated May 18, 2009 From the International Searching Authority Re.: Application No. PCT/IL2008/001685.

Agostini et al. "Evaluation of Feature-Based Registration in Dynamic infrared Imaging for Breast Cancer Diagnosis", Proceedings of the 28th IEEE EMBS (Engineering in Medicine and Biology) Annual International Conference, New York City, USA, Aug. 30-Sep. 3, 2006, XP031235634, p. 953-956, Aug. 30, 2006. p. 953, § 2, 3.

Aksenov et al. "3D Thermography for Quantification of Heat Generation Resulting From Inflammation", Proceedings of the 8th 3D Modelling Symposium, Paris, France, XP))2523191, 11 P., 2003.

Deng et al. "Enhancement of Thermal Diagnostics on Tumors Underneath the Skin by Induced Evaporation", Proceedings of the 2005 27th Annual International Conference of the Engineering in Medicine and Biology Society, Shanghai, China, Sep. 1-4, 2005, IEEE-EMBS 2005, XP002519610, 7: 7525-7528, 2005. Passage Bridging p. 7526 and p. 7527, Abstract, Figs.4, 5.

Deng et al. "Mathematical Modeling of Temperature Mapping Over Skin Surface and its implementation in Thermal Disease Diagnostics", Computers in Biology and Medicine, XP002523192, 34(6): 495-521, Sep. 2004. Abstract, p. 497.

Kaczmarek et al. "Optical Excitation Methods in Active Dynamic Thermography in Medical Diagnostics", Proceedings of the SPIE—The International Society for Optical Engineering SPIE, XP002519609, 5566(1): 120-126, 2004. p. 121, Last §, p. 123, First §, Fig.3.

Lipari et al. "Advanced Infrared Image Processing for Breast Cancer Risk Assessment", Proceedings of the 19th Annual International Conference of the IEEE/EMBS Engineering in Medicine and Biology Society, Chicago, IL, USA, Oct. 30-Nov. 2, 1997, XP010325780, 2: 673-676, Oct. 30, 1997. Abstract, Sections II, III, Fig.3.

Moderhak et al. "Problems of 3D Breast Imaging", Gdansk University of Technology, Department of Biomedical Engineering, 2 P.

Tan et al. "A Novel Cognitive Interpretation of Breast Cancer Thermography With Complementary Learning Fuzzy Neural Memory Structure", Expert Systems With Applications, XP005919120, 33(3): 652-666, Mar. 13, 2007. Abstract, p. 658-659, Section 4, Fig.5.

International Preliminary Report on Patentability Dated Jul. 15, 2010 From the International Bureau of WIPO Re. Application No. PCT/IL2008/001683.

International Preliminary Report on Patentability Dated Jul. 15, 2010 From the International Bureau of WIPO Re. Application No. PCT/IL2008/001685.

International Preliminary Report on Patentability Dated Oct. 7, 2010 From the International Bureau of WIPO Re. Application No. PCT/IL2008/001684.

Written Opinion Dated Jun. 2, 2009 From the International Searching Authority Re.: Application No. PCT/IL2008/001683.

Response Dated Jun. 21, 2011 to Communication Pursuant to Article 94(3) EPC of Dec. 21, 2010 From the European Patent Office Re. Application No. 08866783.7.

Communication Pursuant to Article 94(3) EPC Dated Aug. 16, 2011 From the European Patent Office Re. Application No. 08873559.2.

International Search Report Dated Jun. 2, 2009 From the International Searching Authority Re.: Application No. PCT/IL2008/001683.

Bichinho et al. "A Computer Tool for the Fusion and Visualization of Thermal and Magnetic Resonance images", Journal of Digital imaging [Online], XP002527797, Retrieved From the Internet: URL:http://www.springerlink com/content/5w157t2747272m65/>. p. 3, col. 1, Line.5-col. 2, Line 6, Fig.1.

Communication Pursuant to Article 94(3) EPC Dated Jan. 12, 2011 From the European Patent Office Re. Application No. 08867385.0.

Response Dated Jul. 12, 2011 to Communication Pursuant to Article 94(3) EPC of Jan. 12, 2011 From the European Patent Office Re. Application No. 08867385.0.

Translation of Office Action Dated Jun. 22, 2011 From the State Intellectual Property Office of the People's Republic of China Re. Application No. 200880127685.9.

Communication Pursuant to Article 94(3) EPC Dated Feb. 8, 2012 From the European Patent Office Re. Application No. 08867385.0.

Communication Pursuant to Article 94(3) EPC Dated Oct. 18, 2012 From the European Patent Office Re. Application No. 08873559.2.

Office Action Dated Dec. 2, 2012 From the Israel Patent Office Re. Application No. 206644 and Its Translation Into English.

Official Action Dated Oct. 15, 2012 From the US Patent and Trademark Office Re. U.S. Appl. No. 12/934,647.

Translation of Office Action Dated Feb. 22, 2012 From the State Intellectual Property Office of the People's Republic of China Re. Application No. 200880127684.4.

Barone et al. "A Biomedical Application Combining Visible and Thermal 3D Imaging", INGEGRAF (Asociacion Espanola dc Ingcnieria Grafica) 2006, Retrieved From the Internet, p. 1-9, 2006.

Wikipedia "Surface Integral", Wikipedia, the Free Encyclopedia, Retrieved From the Internet, 3 P., Jan. 23, 2012.

Official Action Dated Jan. 25, 2013 From the US Patent and Trademark Office Re. U.S. Appl. No. 12/811,099.

Translation of Notice of Reason for Rejection Dated Dec. 21, 2012 From the Japanese Patent Office Re. Application No. 2010-541136.

Translation of Notice of Reason for Rejection Dated Dec. 21, 2012 From the Japanese Patent Office Re. Application No. 2010-541137.

Sato et al. "Image Guidance of Breast Cancer Surgery Using 3-D Ultrasound Images and Augmented Reality Visualization", IEEE Transactions on Medical Imaging, 17(5): 681-693, Oct. 1998.

Communication Pursuant to Article 94(3) EPC Dated Apr. 25, 2013 From the European Patent Office Re. Application No. 08867385.0.

Wedemeyer et al. "Numerical Simulation of the Three-Dimensional Structure and Dynamics of the Non-Magnetic Solar Chromosphere", Astronomy & Astrophysics, 414(3): 1121-1137, Feb. 2004.

Office Action Dated Sep. 8, 2013 From the Israel Patent Office Re. Application No. 206663 and Its Translation Into English.

Translation of Decision on Rejection Dated Aug. 6, 2013 From the State Intellectual Property Office of the People's Republic of China Re. Application No. 200880127684.4.

Office Action Dated Oct. 20, 2013 From the Israel Patent Office Re. Application No. 208274 and Its Translation Into English.

Office Action Dated Oct. 31, 2013 From the Israel Patent Office Re. Application No. 206644 and Its Translation Into English.

* cited by examiner

SYSTEM AND METHOD FOR REGISTRATION OF IMAGING DATA

RELATED APPLICATIONS

This Application is a National Phase of PCT Patent Application No. PCT/IL2008/001683 having International filing date of Dec. 28, 2008, which claims the benefit of U.S. Provisional Patent Application No. 61/006,223 filed on Dec. 31, 2007. The contents of the above Applications are all incorporated herein by reference.

FIELD AND BACKGROUND OF THE INVENTION

The present invention relates to systems and methods for enabling medical imaging data registration and more particularly, to systems and methods which enable registration of tissue imaging data for the purposes of enhancing diagnostic resolution.

Medical imaging is routinely used to image the human body or portions thereof for clinical or research purposes.

For over 70 years, medical imaging had almost exclusively depended on conventional film/screen X-ray imaging. However, in the last 40 years, medical imaging has experienced major technological growth which has resulted in the development and commercialization of new imaging technologies. Such technologies, which include X-ray Computed Tomography, Magnetic Resonance Imaging, Digital Subtraction Angiography, ultrasound, thermography and nuclear emission imaging (e.g. PET, SPECT, etc.) are now routinely used in detection and diagnosis of disease.

The availability of such diagnostic technologies provides a physician with a range of diagnostic tools to choose from and also potentially enables correlation (registration) of several different imaging approaches thus greatly enhancing accuracy of diagnosis.

Having a range of diagnostic tools to choose from can potentially enhance the ability of a physician to diagnose a disease, however, it is the correlation of results from several imaging approaches which has the greatest potential in enhancing diagnostic accuracy.

Although a patient can be subjected to multiple imaging approaches (e.g. x-ray and ultrasound), the images obtained are not easily registered or correlated with one another. Differences in scale, position, or in the orientation of the imaging plane are almost inevitable. With certain tissues (e.g. breast) imaging registration is further hampered by deformation of the tissue which can result from the imaging technique (e.g. compression of breast tissue between mammography plates).

The prior art is replete with approaches for enabling registration of medical images, most requiring the use of orientation markers or models which are typically constructed using 3-D imaging approaches (e.g. MRI).

Prior art registration approaches are typically designed for registering imaging data obtained by x-ray, ultrasound or MRI. However, in the case of thermographic imaging, such approaches are incapable of providing an accurate registration since thermographic data is derived from the surface of the imaged body portion rather than the internal tissues.

A thermographic image is typically obtained by collecting from the a body of the subject radiation at any one of several infrared wavelength ranges and analyzing the radiation to provide a two-dimensional temperature map of the surface. The thermographic image can be represented as a visual image with or without corresponding temperature data. The output from infrared cameras used for infrared thermography typically provides an image comprising a plurality of pixel data points, each pixel can provide relative temperature information which is visually displayed, using a color code or grayscale code. This information can be further processed by computer software to generate for example, mean temperature for the image, or a discrete area of the image, by averaging temperature data associated with all the pixels or a subcollection thereof.

Since shifts in body temperature can indicate the presence of a disorder, (e.g. inflammation caused an increase in temperature), a thermographic image can be used by a physician to determine whether or not a site includes presence of a disorder.

While reducing the present invention to practice, the present inventors have uncovered that surface contour data, especially when combined with thermal imaging data can be used for registration of imaging modalities.

SUMMARY OF THE INVENTION

The present invention provides a method of obtaining imaging data from a tissue region comprising (a) obtaining a first surface contour of the tissue region in a first state (b) obtaining a first imaging data from the tissue region in the first state and associating it with the first surface contour (c) obtaining a second surface contour of the tissue region in a second state; (d) using the first surface contour and the second surface contour to model the tissue region at the second state; and (e) transforming the first imaging data into a second imaging data associated with the tissue region in the second state.

According to preferred embodiments of the present invention, the imaging data is thermal imaging data.

According to preferred embodiments of the present invention, the imaging data is X-ray imaging data.

According to preferred embodiments of the present invention, the imaging data is ultrasound imaging data.

According to preferred embodiments of the present invention, transforming the imaging data is effected by correcting an imaging plane of said first imaging data according to the model.

The present invention successfully addresses the shortcomings of the presently known configurations by providing a simple and yet highly effective approach for registering imaging data.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-D schematically illustrate systems for image registration constructed in accordance to the teachings of the present invention system.

Figure 2:
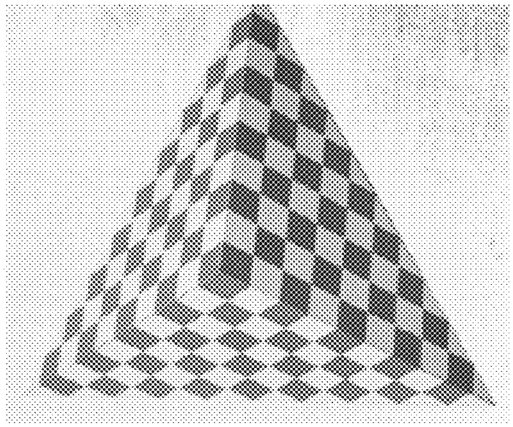

FIG. 2 illustrates a triangular pyramid with a surface checkerboard pattern which can be used as a calibration target for the system of the present invention.

Figure 3:
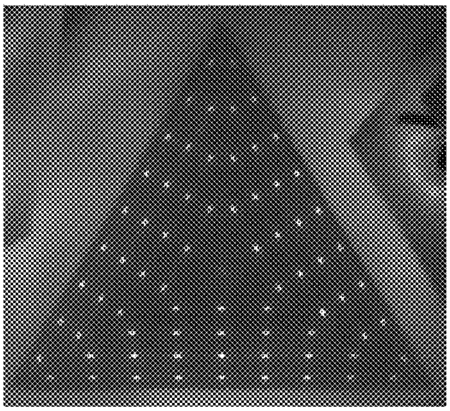

FIG. 3 illustrates a calibration target which can be used to calibrate a thermal imaging camera of the system of the present invention.

Figure 4:
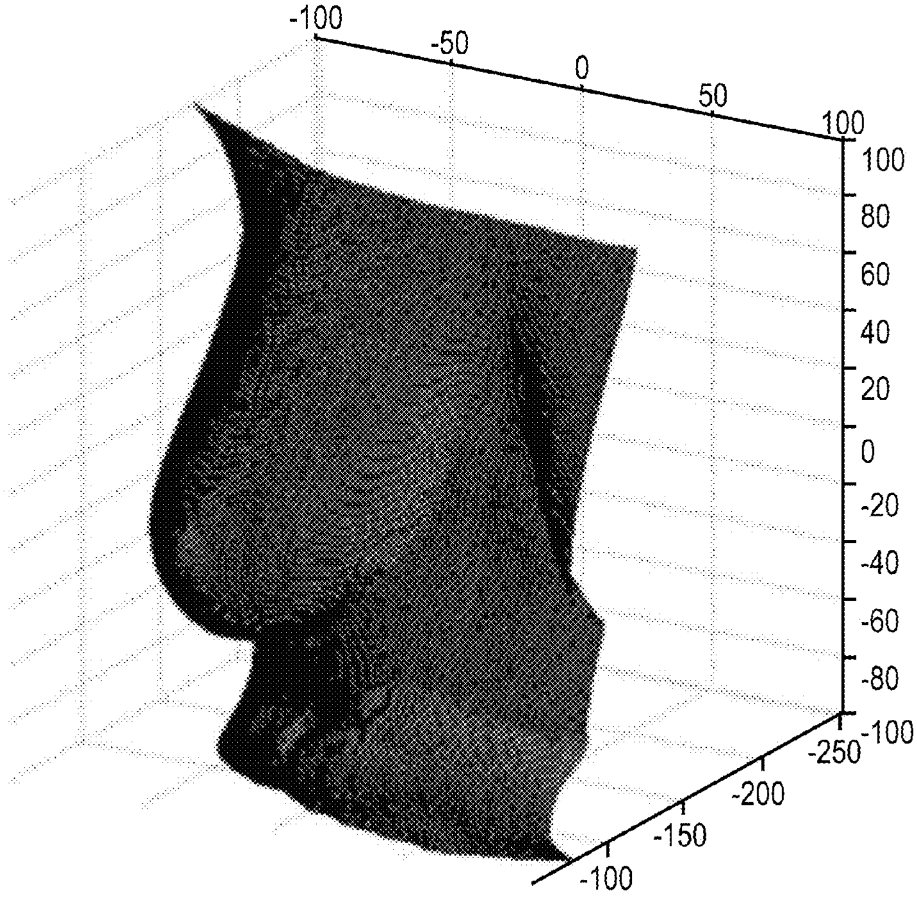

FIG. 4 illustrates a three dimensional contour model of a female breast as constructed by using the system of the present invention.

Figure 5:
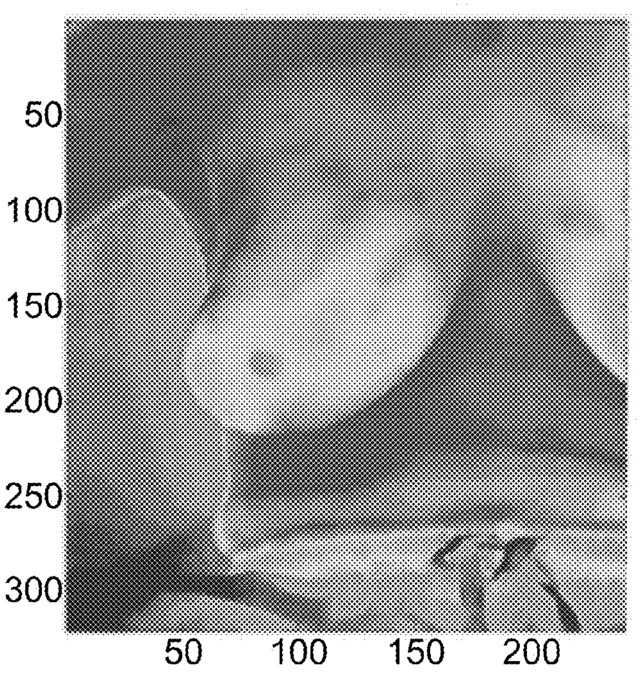

FIG. 5 illustrates a thermal image captured by the thermal camera utilized by the present invention.

Figure 6:
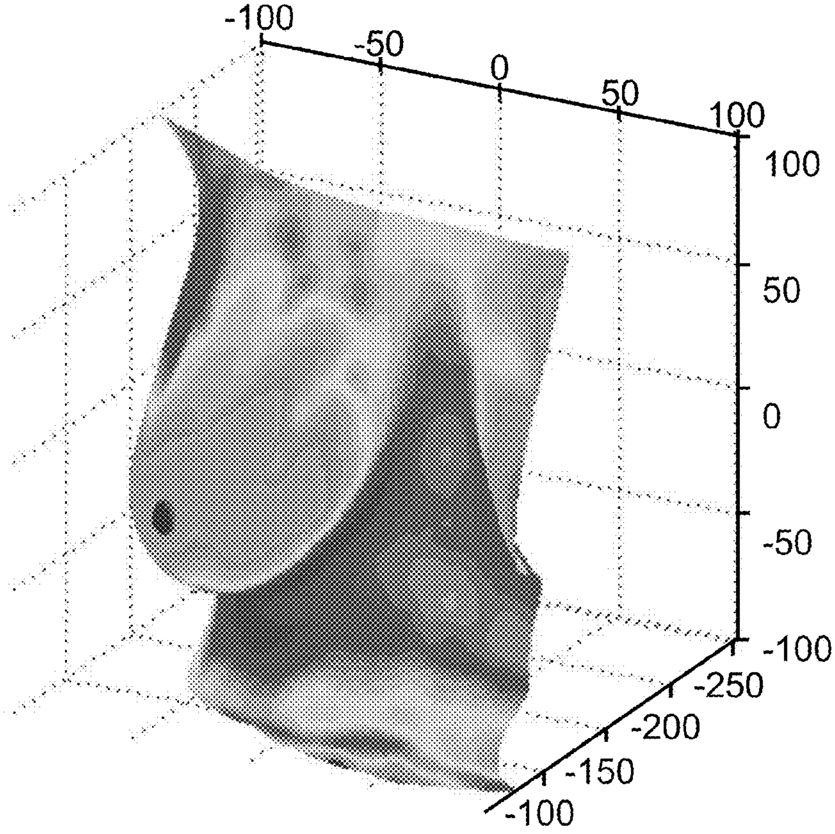

FIG. 6 illustrates superimposition of thermal data on a three dimensional contour model of a female breast as constructed by the system of the present invention.

DESCRIPTION OF THE PREFERRED EMBODIMENTS

The present invention is of a system and method which can be used imaging data registration and correlation of data obtained by several imaging modalities.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Medical imaging offers numerous imaging modality options for enabling diagnosis of a patient. However, since images obtained by such modalities are not easily registered or correlated with one another, oftentimes diagnosis relies upon use of a single imaging modality or on the ability of a physician to correlate between various imaging data.

Differences in scale, position, or in the orientation of the plane of projection (of a two-dimensional image) are inevitable, making free correlation between images nearly impossible. With certain tissues (e.g. breast) imaging registration is further hampered by deformation of the tissue which can result from the imaging technique (e.g. compression of breast tissue between mammography plates).

While reducing the present invention to practice, the present inventors have devised a simple, yet effective approach for medical imaging registration. Such an approach can be used to register imaging modality data taken at any time and under any settings thus enabling correlation between historical as well as previously non-relatable imaging data.

Thus, according to one aspect of the present invention there is provided a method of obtaining imaging data from a tissue region.

As used herein, the phrase "tissue region" refers to any region of tissue in a body, including regions defining an organ, a limb or an anatomical region of interest. Preferably, the surface of the tissue region or a portion thereof has a contour which can be mapped via, for example, light imaging (in the case of external, i.e. skin-juxtaposed tissue regions) or via other imaging techniques (e.g. thermal imaging in the case of a tissue region having a surface disposed within the body).

The method of the present invention is effected by associating surface contour data of the tissue region in a first state with imaging data from the tissue region in the first state.

As used herein the phrase "imaging data" refers to data obtained by an imaging approach. Such data can be in the form of two dimensional or three dimensional data files which can be processed and presented on a display such as a computer screen. Such data can be ultrasound data, x-ray data, magnetic imaging data, nuclear medicine data, thermographic data, optical imaging data, electrical impedance data, optoacoustic imaging data, elasticity data, microwave imaging data and the like.

Surface contour information can be collected using any one of several approaches. In the case of skin-protruding tissue regions (e.g. breast), the contour of the skin can be mapped using a imaging device (e.g. a CCD or CMOS visible light camera) and projected or applied color and/or geometrical patterns (for further description see the Examples section below). Skin contour information can also be obtained using a coordinate-measuring machine (www.en.wikipedia.org/wiki/Coordinate-measuring_machine).

In any case, once surface contour information is obtained, it is processed to yield a three dimensional model of the surface contour as is shown, for example, in FIG. 4. Such a contour model represents the three dimensional appearance of the tissue region and thus can be used as a reference map for imaging data obtained from the tissue within the tissue region.

The same tissue region is also imaged using a modality such as ultrasound, MRI, CT and the like in order to obtain imaging data. It will be appreciated that this step of the present methodology can be effected prior to, concomitantly with or following the step of obtaining surface contour information.

In any case, the surface contour information and the imaging data are collected in a manner which enables correlation between the surface contour of the tissue region and the data obtained via imaging. One approach which can be used to enable such correlation involves the use of calibration targets. Such targets provide one or more points of reference which can be used to map the spatial orientation of the captured contour and imaging data and thus calibrate the devices used for surface contour capture with the imaging modality device/system. Use of calibration targets is further explained in detail in the Examples section which follows with respect to contour data obtained via visible light imaging.

Use of calibration targets enables either calibration of the devices used in contour and imaging data capture, in which case, the position and orientation of these devices can be calibrated such that they image the same plane and region, or alternatively, such calibration can be used to correct the contour or imaging data by mapping them to the same points of reference. In any case, once the devices or images obtained thereby are calibrated, images obtained thereby are fully correlatable and can be used to provide a combined image (see FIG. 6).

For example, correlating ultrasound data with surface contour data can yield information which can be used to correlate US imaging with imaging obtained by other modalities (e.g.

thermography, X-ray). A standard US image is embodied by a two dimensional plane defined by the ultrasound wave plane transmitted from a transmitter in the US probe. The ultrasound wave is reflected by body tissue back to a receiver, usually also located within the probe. The ultrasound waves propagate in a manner determined by the location and angle of the probe; the probe location also determines which plane in the body is imaged. Therefore, if the relationship between the angle of the probe, the direction of wave plane emitted from it and the position of the probe is known at the time the image is obtained, the position of the image plane with respect to the body can be determined.

Since the US probe is manually positioned on the body and since contact between the probe and the skin (which is required for imaging) leads to contour deformation, the plane of an US image varies from one image capture to another. As a result, for each image, a different geometric structure of the tissue is captured. Correlating such images to a single tissue region/structure can be effected by applying deformation functions based on deformation models. These models can be applied to spatial locations inside a tissue, in addition to spatial locations on the surface.

By qualifying the state of a tissue region (e.g. the deformation state) using the 3-D (contour) modeling described herein and associating the position and/or state with the imaging data (e.g. US image planes) one can a correlate between several image planes taken at different tissue states. Correlation can be made between a reference 3-D image and each US image by means of deformation conversion and thus each US image plane can be correlated with a location in the 3-D image and thus the location in the tissue region.

Once an imaging modality is correlated with surface contour data obtained using the present invention, any shift in the surface contour of the tissue region (i.e. shift in state) can be used to 'correct' the imaging data.

The calibration target must posses several characteristics to enable co-calibration of the surface and imaging data.

(i) It must be 'visible' to the devices used in acquisition of the surface a contour and imaging data; e.g. the spatial reference points provided on the target should be included in the data obtained thereby.

(ii) it must accurately determine the spatial location and angle (imaging or projection) of the devices.

(ii) the data obtained thereby must be correlatable with preacquired 3-D data (e.g. MRI data).

Medical imaging data includes a collection of data points of interest (e.g. data points representing abnormal tissue such as a tumor mass). A physician's main concern when comparing various imaging modalities is the shift or movement of tissue or imaging data that occurs between different modalities or through acquisition of the same imaging data at several different time points. Specifically, data points of interest do not appear at the same region of an image when different planes of tissue are imaged and/or when the tissue region is subject to different forces which can result from different imaging positions and the like.

Thus, effective registration of imaging modalities must take into account tissue deformation as well as imaging planes for effective image registration.

By mapping the imaging data to surface contour data, the present invention enables effective yet simple image registration as well as correction of imaging data for tissue deformation and matching of imaging modalities taken from different angles and positions.

Such correction or registration of imaging data can be further enhanced by employing a tissue deformity model which can be related to the contour data obtained by the present approach. Such supplementary deformity correction can be applicable in cases where the tissue imaged is deformed by the imaging device (e.g. mammography device) and the tissue within the tissue region does not exhibit uniform deformity due to the heterogeneity of the tissue.

Tissue deformation models are well known in the art, examples include the Finite Element method and the Linear Elasticity theory. Such models can be used to further enhance the correction of data point positions within the tissue by compensating for varying deformation of various tissues within the tissue regions.

Such data can also be acquired by combining 3-D contour acquisition along with thermal imaging. This can be achieved by capturing a plurality of thermal images (preferably from different angles) from a tissue region (e.g. breast) at a first state and determining the positions of several thermal landmarks within the tissue (landmarks that are easily recognizable and are homogenously spaced throughout the tissue are preferred). The same images can then be captured when the tissue is subjected to controlled deformation (i.e. the tissue region is in a second state) and the position of the landmarks determined again. By comparing the positions of the landmarks in both states, a map of relative tissue compliance (to applied force) can be constructed for the individual imaged. Such a map can be used to model the tissue within the tissue region and predict shifts of discrete locations within the tissue region as the tissue region deforms.

The present invention can be used to correct and register data obtained from any imaging modality. One specific modality which can benefit from the present approach is thermal imaging.

Thermal imaging can be used to image both external and internal tissue regions; it provides a highly accurate and sensitive temperature map and thus pathological state of the tissue region of interest.

Tissues routinely imaged via thermal imaging devices include breasts, blood vessels and muscles as well as internal organs.

When applied to thermal imaging registration, the present approach enables superimposition of thermal imaging data onto the surface contour data obtained as described herein. Such superimposition provides two benefits registration of the thermal imaging data and such an ability to correlate such data with data obtained from other imaging modalities (as is described hereinabove) and a more accurate correlation between the (imaged) surface thermal data and the actual internal source of this data.

A thermal camera captures two dimensional images. Its output corresponds to the number of photons which strike its detectors. An electric signal is generated according to the number of incident photons. The camera 'translates' this signal to a numerical value which can represent temperature values or relative gray level values.

In a 2D thermal image of a 3D object, pixels corresponding to slanted areas (situated in an angle relative to the camera) are lacking information because the infrared radiation is emitted from a larger area detected by the camera and which is unknown to it.

In the present approach, a further connection between the values obtained from the thermal camera and the observed object is made, further enhancing the 2D information acquired from a standard thermal image. As is further described herein, a thermal camera is calibrated with a 3D imaging system and 3D and thermal images of an object are obtained (see Examples section below). Calibration allows matching of pixel value from the 2D thermal image to the corresponding area in the 3D object. This area is often larger than the size of one pixel so the information is matched up with a larger area, according to the information from the 3D object. This reflects the object's emission more accurately since the 3D structure is taken into account and what appears to be a single pixel of a 2D thermal image is correlated with the true area size thus yielding additional thermal information.

The present methodology can be carried out using a system having software and hardware components.

FIGS. 1*a-d* illustrate a system for registration of imaging data which is referred to herein as system 10. System 10 is described in context with breast imaging, however, it should be noted that system 10 of the present invention can also be used in diagnosis of other body regions, including for example, stomach, back and the like.

Figure 1A:
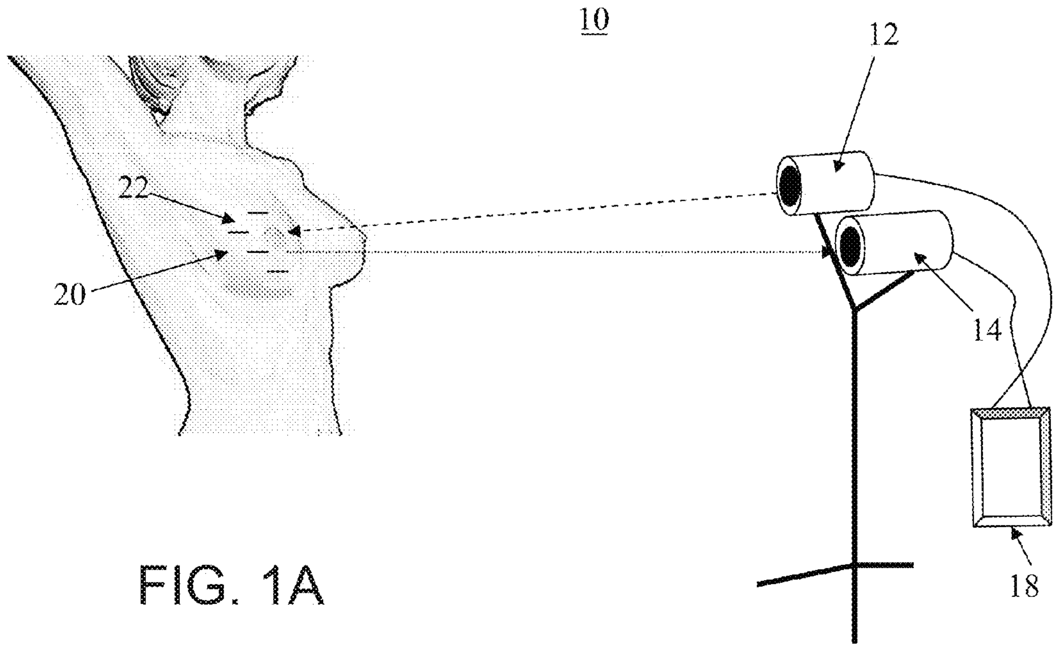

As is shown in FIG. 1*a*, system 10 includes a projector 12 and a visible light camera 14. System 10 further includes a processing unit 18 which is in communication with projector 12 and camera 14. Processing unit 18 is configured for communicating a projected pattern to projector 12 while acquiring and processing data captured by camera 14. In that respect, processor 18 stores the projection files and executes software which enables data collection and processing. To that effect a software suite such as MatLab™ can be configured for processing the captured images in order to generate the contour model.

The components of system 10 can be included in a single housing or provided as individually housed, yet interconnected devices.

Prior to imaging data acquisition, system 10 is calibrated using a calibration target (exemplified in FIG. 2) as is described in Example 1 of the Examples section hereinbelow such that projector 12 and camera 14 are co-aligned. Following calibration, system 10 is then utilized to capture image information from the target tissue (breast 20 shown in FIG. 1*a*). The image information captured by camera 14 includes a plurality of captured frames each including a different pattern 22 projected on the surface of the tissue region. The captured frames are then processed by processing unit 18 to yield 3-D contour data (an example of which is shown in FIG. 4.

Following setup, system 10 can be utilized along with any imaging modality to thereby enable registration of imaging data.

Figure 1B:
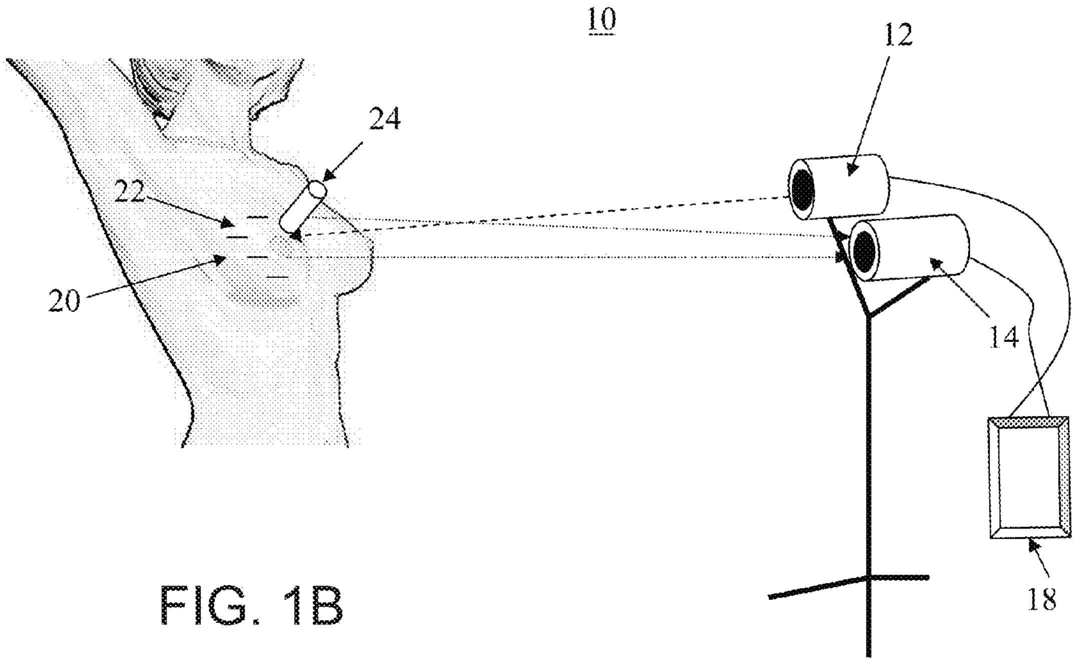

FIG. 1*b* illustrates use of system 10 in registering image data acquired by an ultrasound probe.

Breast contour data is acquired as described above and a breast contour model is generated prior to ultrasound imaging. An ultrasound probe 24 is then used to scan breast tissue and acquire one or more images at one or more US scanning planes. For each image/plane, system 10 acquires information which includes the contour of the breast as deformed by the ultrasound probe and the angle and thus projection plane of the ultrasound probe and therefore the plane of acquired ultrasound image.

The data collected prior to and during ultrasound imaging can then be used to correlate the ultrasound images to the contour model and correct the ultrasound images obtained to the non-deformed breast model obtained prior to the ultrasound exam.

Figure 1C:
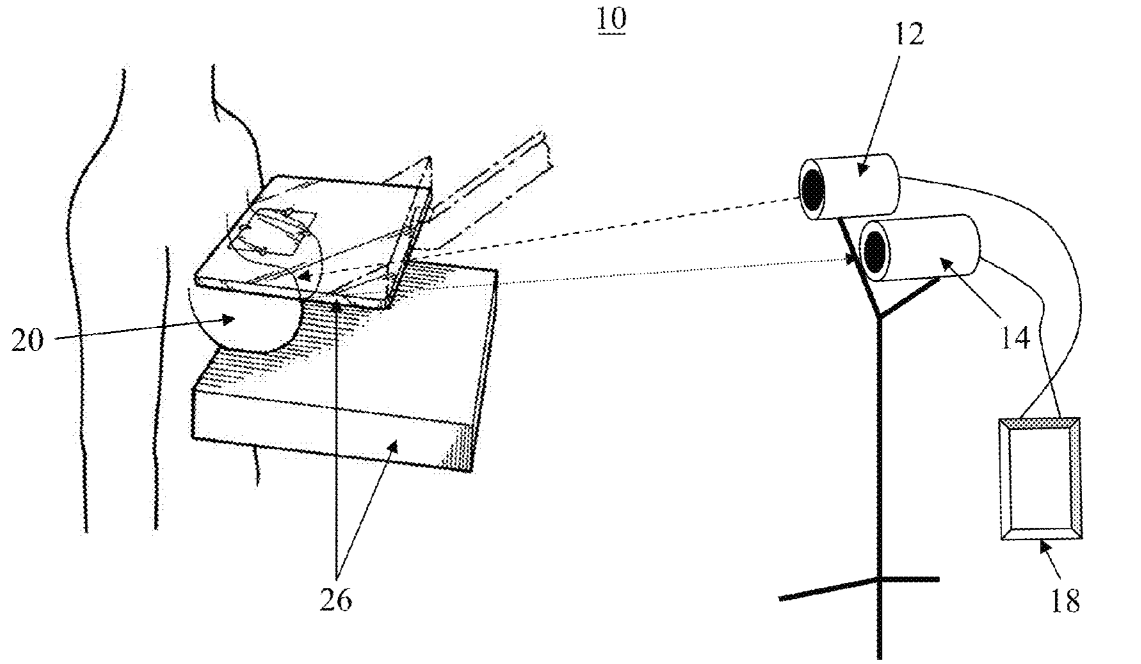

FIG. 1*c* illustrates use of system 10 in registration of image data acquired by an X-ray imager.

In X-ray imaging of the breast (mammography), the breast tissue is compressed between plates and thus is deformed. Prior to breast compression, Breast contour data is acquired as described above and a breast contour model is generated.

Following generation of such a model, breast 20 is compressed between mammography plates 26 and an x-ray image of the breast is then acquired. Breast 20 is also imaged using system 10 and a contour model is generated for breast 20 at the deformed state. The contour model can take into account the plates and their respective positioning in order to enhance contour modeling.

Contour model of deformed breast 20 can then be correlated with the acquired x-ray data and corrected according to the contour data acquired prior to breast 20 compression.

Figure 1D:
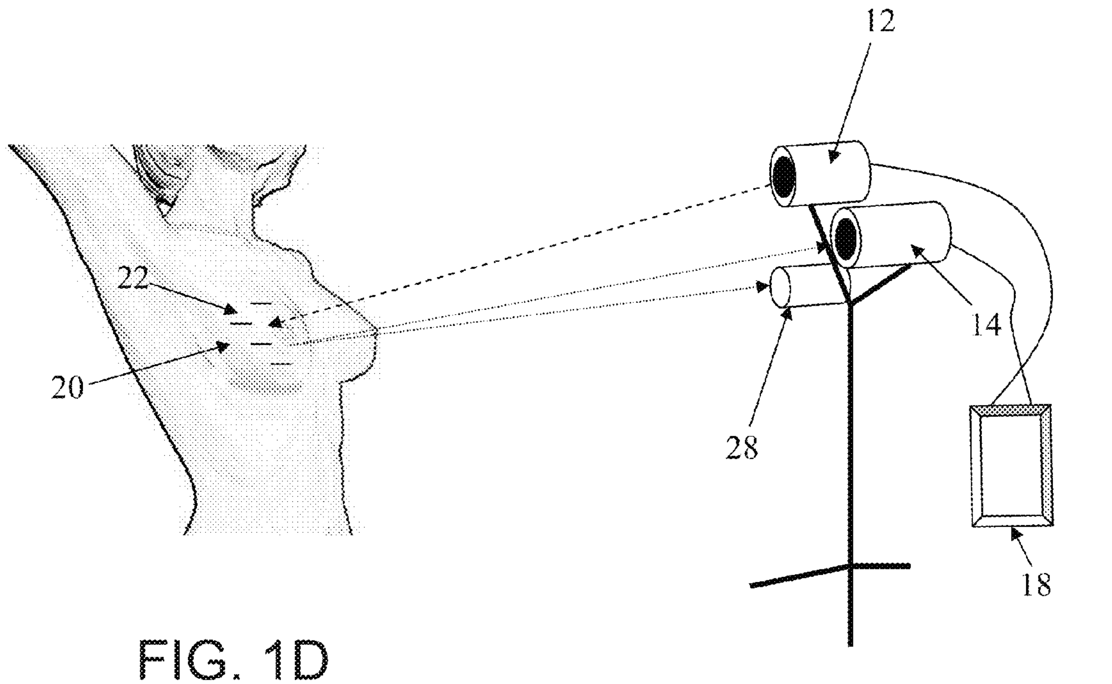

FIG. 1*d* illustrates use of system 10 in registration of image data acquired by a thermal imaging device.

In such a configuration, system 10 utilizes a calibration target which is sensitive to both camera 14 and thermal imaging device 28. Such a calibration target is exemplified in FIG. 3.

Once all the devices in the system are calibrated to the same axis (camera 14, projector 12 and thermal imaging device 28) and a contour model of the breast is acquired, thermal imaging device 28 is utilized for thermal image capture and an a combined image of thermal data superimposed onto contour data is generated by processing unit 18 (described in detail in the examples section which follows.

Thus, data acquired by the above described imaging approaches is integrated with the co-acquired contouring data and used for data correction, thus enabling correlation between various imaging modalities which are acquired using system 10 of the present invention.

For example, imaging data acquired via US (along with system 10) can be corrected (e.g., adjusted in as far as imaging plane, depth etc.) using the 3-D contour model (generated by system 10) and the corrected imaging data can then be correlated with similarly corrected thermal or X-ray data. Similarly, thermal data acquired while using system 10 of the present invention can be registered with X-ray data for the purpose of, for example, diagnosis of breast cancer.

It will be appreciated that correction of imaging data can be effected such that the corrected data represents the tissue region at a single normalized state (for example, in the case of breast tissue such a state can be that observed in an upright subject), or alternatively, correction can be effected such that the imaging data acquired by one approach is corrected to represent the tissue state (deformation state) of a tissue imaged using a second approach. For example, X-ray data if provided on film and thus cannot be easily manipulated can be compared to a US image which is corrected such that the corrected US image represents tissue imaged under a deformation state (e.g. compressed within plates) identical to that of X-ray imaging.

In any case, such co-registration of imaging data, which can be effected manually by simply superimposing two registered images (as software files or hard copies) or computationally, by integrating imaging data and isolating data points of interest, enables a treating physician to verify the existence of pathologies with increased confidence thus greatly enhancing diagnostic accuracy.

Although the present method has been described in the context of medical imaging, it will be appreciated that the present method and system find use in other fields including, for example, mechanical engineering and the like.

It is expected that during the life of this patent many relevant imaging modalities will be developed and the scope of the term imaging data is intended to include data obtained by such new technologies a priori.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Contour Model with Superimposed Thermal Data

A model of the surface contour of a female breast was generated and utilized to map thermal data thereupon.

Material and Methods

Three dimensional contour data was obtained using a projector (Mitsubishi electronics model XD206U) and a camera (Pixelink model PL-B741F). A thermal image was obtained using a thermal camera (FLIR model PHOTON OEM).

In order to obtain superimposed thermal data on a surface contour, the thermal and visible light cameras must are co-calibrated using a single calibration target. It is only necessary to calibrate the system once following which the location of each of the devices is fixed. The calibration of the cameras (video and thermal) is achieved by correlating pixels present in images captured by these cameras with known spatial reference points. Similarly, the projector is calibrated by correlating projected pixels with such spatial reference points. In order to reconstruct the three dimensional feature of an object, images of patterns projected by the projector on the object are captured by the camera and the pixels of the captured image are analyzed (as is further explained hereinafter) and matched with the spatial reference points.

The spatial reference points selected for calibration can be presented on a calibration target such as a triangular pyramid with a surface checkerboard pattern (FIG. 2).

Calibration of the devices is effected as follows. A point of origin is selected on the calibration target, e.g. the point protruding out in the middle of the pyramid (FIG. 2). The reference points for calibration of the video camera are the square's corners; the reference points selected for the thermal camera are the square centers.

In the image captured, each reference point is characterized by a set of pixel coordinates (u, v). Their spatial coordinates (x, y, z) are known, relative to the origin defined. Both coordinates can be represented by homogeneous coordinates for simplification of calculations. A calibration matrix, P, is constructed by correlating between the pixel coordinates (u, v) and their spatial locations (x, y, z). This matrix solves the following equation:

$$\begin{pmatrix} u \\ v \\ 1 \end{pmatrix} = P \cdot \begin{pmatrix} x \\ y \\ z \\ 1 \end{pmatrix}$$

Its size is (3, 4) and therefore it includes 12 elements which are composed of the device's intrinsic parameters (pixel size, focal length etc.) and extrinsic parameters (device's location; angles and displacement compared to selected origin in space). In addition, the matrix includes perspective implementation.

Although the matrix contains 12 elements, there are only 11 unknown parameters (5 intrinsic and 6 extrinsic). As is evident from the equation above, each (x, y, z) point provides two coordinates in an image (u and v) and two separate equations, one for each pixel coordinate. To calibrate each camera, only one image of the calibration target is required. In this image, 6 pixels are selected to solve the 12 equations and the 12 elements of the matrix P are extracted. In reality, more than 6 points are selected in the image to obtain higher precision.

The thermal camera is calibrated using the same process as the video camera by correlating pixels in an image to spatial locations, solving the equations and constructing a calibration matrix. The difference between the thermal camera and the video camera is that when calibrating the thermal camera, the pixels are selected from a thermal image and the reference points on the calibration target are thermally visible. In the present system, the reference points selected for calibration of the thermal camera are the square centers on the checkerboard pattern, on the same triangular calibration target utilized for calibration of the video camera.

Several approaches can be used in order to make such points visible to the thermal camera:

Using Thermoelectric Coolers (TECs) which when connected to a direct current source generate a temperature differential detectable by the thermal camera.

Using heat generating electrical resistors in the calibration target.

Coating the calibrating target with materials with significantly different emissivity, thereby producing a pattern of dark and light squares.

A calibration target modified for use with a thermal imaging camera is illustrated in FIG. 3.

Calibration of the projector is also obtained by matching up its pixels with spatial reference points. Since the projector projects pixels rather than capturing them defining its pixels requires a more complex procedure. Calibration of the projector is achieved by projecting specific patterns on the calibration target and capturing all patterns with the video camera (coded light approach). By doing so, each of the projectors' pixels is assigned a unique code. This enables correlation between the projector's pixels, to the images obtained by the camera. Different light codes can be utilized for this procedure. In our system we use the binary Gray code which consists of patterns of dark and light stripes to perform three dimensional surface imaging [Sato and Inokuchi, J. of Robotic Systems 2(1) 27-39; 1985]. When a sequence of horizontal and vertical Gray code patterns are projected on the calibration target and captured by the camera, each pixel attributed to the projector possesses its own binary code composed of ones and zeros. When the Gray code is utilized, the number of patterns required for projection depends on the number of pixels in the projector. Thus, if the projector has 1024 pixels (210), 10 gray code patterns are projected so that each pixel has its unique sequence. Now that the pixels can be identified, the procedure of corresponding them to points in the world with known locations, solving equations and defining the calibration matrix is carried out while the reference points selected are the squares corners on the calibration target (as with the video camera).

When all three calibration matrices are obtained, one for each device, they can be used to associate points in a two dimensional image with a three dimensional structure. The devices are fixed in position relative to each other since their matrices are constructed in accordance with, amongst other parameters, their positions and angles.

RESULTS

The projector was utilized to sequentially project multiple light patterns onto a female breast while the camera (having a known position with respect to the projector) was utilized to capture reflected patterns. The light patterns projected was a sequence of Gray code patterns which provide each pixel with a unique sequence of ones and zeros. These pattern points projected onto the female breast in this case were located in the captured image and used to extract contour information.

Reconstruction of three dimensional data was obtained through Triangulation. The camera and projector were placed side by side (as opposed to one on top of the other) such that the projector projected vertical stripes (Gray code patterns) and the triangulation was implemented in a horizontal manner. The basis for triangulation lies in the triangle formed by the intersection of a camera image pixel with a plane from the projector (a plane because stripes and not dots are projected). Each camera pixel intersects with a plane projected from the projector at a specific point in space, on the surface of the projected object.

In the present system triangulation is facilitated by correlating the camera's pixels (u, v) and their point of origin from the projector which is known from the projected patterns. Each spatial was attributed to camera pixels by selecting a (u, v) pixel and examining its Gray code, as seen in the image captured by the camera. The result of the Triangulation calculation was the point's spatial location (x, y, z).

Spatial points reconstructed into three dimensional information are only those which are in both the camera's and the projector's field of view.

Using the above described approach, the present inventors constructed a three dimensional contour model of a female breast (FIG. 4).

Once the contour model was obtained, the thermal camera was calibrated as described above and utilized to capture thermal data from breast tissue.

Every object with a temperature above absolute zero emits radiation. The amount of radiation emitted depends on the object's temperature and emissivity. The emissivity of a material is the ratio of energy radiated by the material to energy radiated by a black body at the same temperature. The human skin has high emissivity and is considered close to 1. The amount of radiation emitted by an object increases with its temperature and so an object's temperature can be analyzed by thermal imaging. A thermal Imager detects and displays surface temperatures only, which can be represented as grayscale or color images. It is common in a grayscale image that hot things appear whiter and cooler things appear blacker, although this depends only on the device's settings.

A thermographic camera is a device which converts thermal infrared radiation emitted (and also reflected) by objects into images that can be graphically displayed. Its function is similar to an ordinary digital camera which produces images by detection of visible light. Instead of the 400-750 nanometer range of visible light, infrared cameras operate in wavelengths from 750 to as long as 14,000 nm (14 μm) so their lens must be transparent to infrared radiation (various cameras are sensitive to different wavelength ranges of the infrared region and not the whole infrared region). Humans at normal body temperature radiate most strongly in the infrared range at wavelengths around 10 μm. As with any digital camera, the radiation is focused by optics onto infrared detectors which are responsive to infrared radiation. The radiation is converted to electrical signals which are processed and translated into an image that can be viewed on a standard video monitor. The output of the thermal camera is calibrated in units of temperature.

Thermographic cameras include detectors of one of the two types; cooled or un-cooled.

Cooled thermal detectors are based on the quantum effect; a photon strikes the detector and excites an electron with an amount of energy determined by the photon's frequency. Infrared radiation is low in energy so the difference between two energy levels is small and thus the detector is highly prone to thermal noise.

Un-cooled thermal detectors are comprised of materials which respond to heat in different manners; loading of capacitor, change in resistance (bolometers), expansion of gas etc. Un-cooled detectors can be used in room temperature but are usually less sensitive than cooled detectors.

In this example, the present system utilized an un-cooled thermal camera with bolometers (microbolometers) as detectors. When infrared radiation strikes the detectors, their electrical resistance changes. This resistance change is measured and can be processed into temperatures which can be represented graphically. FIG. 5 illustrates the resultant thermal image captured by the thermal camera utilized by the present invention.

This thermal image was then correlated with the 3-D location points (representing a surface) to obtain the (u, v) coordinates in the thermal image which correspond to the (x, y, z) points in space. This in effect results in projection of the 3-D surface onto the image plane of the thermal camera. Once the 3-D location points and the thermal image are co-localized to the same plane, they can be inter-associated. Using interpolation, every (x, y, z) 3-d location is correlated with a value from the thermal image. The values in the thermal image aren't the absolute temperatures of the object, but rather are gray levels which represent the infrared flux emitted from the object and detected by the thermal camera. The resulting image now includes data points which possess four coordinates: (x, y, z, t). The 't' coordinate refers to a numerical value in the thermal image which are added to the 3-d image as color or graylevels points (FIG. 6).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of obtaining thermal data from a tissue region comprising:

(a) obtaining a first surface contour of the tissue region while the tissue region is in a first state;

(b) obtaining a first thermal data from the tissue region in said first state and associating it with said first surface contour;

(c) obtaining a second surface contour of the tissue region while the tissue region is in a second state, different from said first state, said second state corresponding to a deformed shape of the tissue region relative to said first state, said deformation being effected by a non-thermal imaging modality;

(d) processing each of said first and said second surface contours to provide a three dimensional model of the respective surface contour;

(e) transforming said first thermal data into a second thermal data associated with the tissue region in the second state;

(f) obtaining non-thermal imaging data from said non-thermal imaging modality while the tissue region is in said second state; and (g) co-registering said second thermal data with said non-thermal imaging data.

2. The method of claim 1, wherein said tissue region is a breast.

3. The method of claim 1, wherein (a) is effected using at least one camera.

4. The method of claim 1, wherein (a) is effected by capturing an image of a pattern projected onto a surface of said tissue region.

5. The method of claim 4, wherein said pattern is a coded light pattern.

6. The method of claim 4, wherein said image of said pattern is processed using a processing unit.

7. The method of claim 1, wherein said non-thermal imaging modality comprises ultrasound imaging.

8. The method of claim 1, wherein said non-thermal imaging modality comprises x-ray imaging.

9. The method of claim 1, wherein said non-thermal imaging modality comprises magnetic resonance imaging.

10. The method of claim 1, wherein said non-thermal imaging modality comprises at least one of nuclear imaging, electrical impedance imaging, optoacoustic imaging, elasticity imaging and microwave imaging.

* * * * *